US00PP08605P

United States Patent [19]

Christensen

[11] Patent Number: Plant 8,605

[45] Date of Patent: Feb. 22, 1994

[54] ROSE PLANT JACAPRI

[75] Inventor: Jack E. Christensen, Ontario, Calif.

[73] Assignee: Bear Creek Gardens, Inc., Medford, Oreg.

[21] Appl. No.: 817,734

[22] Filed: Jan. 7, 1992

[51] Int. Cl.[5] ..... A01H 5/00

[52] U.S. Cl. ..... Plt./11

[58] Field of Search ..... Plt. 16, 17, 18, 7.1, Plt. 22, 25, 11

*Primary Examiner*—Howard J. Locker
*Assistant Examiner*—E. F. McElwain

*Attorney, Agent, or Firm*—Klarquist, Sparkman, Campbell, Leigh and Whinston

[57] ABSTRACT

A new rose variety is disclosed having an unusual yellow-orange flower color; vigorous, upright growth; abundant glands on upper rachises, stipules, axils, and peduncles; very large, long-lasting blooms; and moderate bloom fragrance. Each bloom, borne singly, has about thirty broad petals. The new variety was created by crossing the medium-red variety Aroheddo with an unnamed deep yellow seedling.

1 Drawing Sheet

1

The present invention relates to a new and distinct variety of rose plant of the hybrid tea class which was originated by me by crossing the medium-red unpatented variety AROheddo with an unnamed deep yellow seedling.

The primary objective of this breeding was to produce a new yellow or orange hybrid tea rose variety having the petal count and flower size of AROheddo combined with the broad petals, vigor and glossy foliage of the unnamed seedling. The primary objective was substantially achieved along with other desirable improvements as evidenced by the following unique combination of characteristics which are outstanding in the new variety and which distinguish it from its parents, as well as from all other varieties of which I am aware:

1. Unusual, distinctive yellow-orange flower color;
2. Vigorous, upright growth;
3. Abundance of glands on upper rachises, stipules and leaf axils, as well as on peduncles;
4. Very large, long-lasting blooms; and
5. Moderate bloom fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Variety AROheddo.

*Pollen parent.*—An unnamed seedling.

Classification:

*Botanical.*—Rosa hybrida.

*Commercial.*—Hybrid tea.

2

FLOWER

Observations made from specimens grown in a garden environment in Somis, Calif., in April–June, 1991.

Blooming habit: Recurrent.

Bud:

*Size.*—The bud is 1½ to 2 inches when the petals start to unfurl.

*Form.*—The bud is long.

*Color.*—When sepals first divide, bud color is Orange Group 24C. When half blown, the upper sides of the petals are Yellow Orange Group 19C, intensifying to Yellow Orange Group 15A nearer the petal base; and the lower sides of the petals are Orange Group 24C at the petal edge, changing to Orange Group 24B near the center of the petal, and finally to Yellow Orange Group 15A near the petal base;

*Sepals.*—Color: Green Group 138D. Surface texture: Covered with fine hairs. There are three normally appendaged sepals edged in numerous glands. There are two unappendaged sepals with hairy edges.

*Receptacle.*—Color: Green Group 143B. Shape: Funnel. Size: Broad, ¼-inch long by ½ inch wide. Surface: Smooth with an occasional hair.

*Peduncle.*—Length: Long, 3 inches. Surface: Glandular. Color: Medium green. Strength: Stiff, erect.

Bloom:

*Size.*—Large. Average open diameter is 5½ inches.

*Borne.*—Singly.

*Stems.*—Long (18 inches), strong.

*Form.*—When first open: High centered. Permanence: Retains its form to the end, outer petals curl back.

*Petalage.*—Number of petals under normal conditions: 30.

*Color.*—The upper sides of the petals are Yellow Orange Group 19C, intensifying to Yellow Orange Group 15A toward the petal bases. The reverse sides of the petals are Orange Group 24D at the petal edges, changing to Orange Group 24C near the center of the petals and finally to Yellow Orange Group 15A near the petal bases. The major color on the upper side is Yellow Orange Group 19C.

*Variegation.*—None.

*Discoloration.*—No change in the general tonality at the end of the first day. Gradual fading is evident at the end of the third day as the flower opens, exhibiting more Yellow Orange Group 19C and less Yellow Orange Group 19A.

*Fragrance.*—Moderate.

Petals:

*Texture.*—Thick and leathery.

*Shape.*—Round.

*Form.*—Tips slightly recurved.

*Arrangement.*—Imbricated, with few petaloids in the center.

*Persistence.*—Drop off cleanly.

*Lastingness.*—On the plant: Long, 6–7 days. As a cut flower: Long, 7–8 days.

Reproductive parts:

*Anthers.*—Size: Large. Quantity: Many. Color: Yellow. Arrangement: Regular round styles mixed with occasional petaloids.

*Filaments.*—Color: Yellow.

*Pollen.*—Color: Gold Yellow.

*Styles.*—Color: Reddish.

*Stigmas.*—Color: Greenish white.

Form: Bush.

Growth: Very vigorous, upright, branching.

Foliage: Number of leaflets on normal mid-stem leaves: 5 or 7.

*Size.*—Large, 6 inches long by 5 inches wide.

*Quantity.*—Abundant.

*Color.*—New foliage: Dark reddish. Old foliage: Upper Surface: Green Group 137C; Lower Surface: Green Group 138B.

*Glandulation.*—There is a profusion of dark red glands in axils where leaflets join the rachis and many glands on the upper surface of the rachis.

Leaflets:

*Shape.*—Pointed oval.

*Texture.*—Upper side: Leathery and glossy.

*Edge.*—Serrated.

*Serration.*—Single and small.

*Petiole rachis.*—Color: Green.

*Petiole underside.*—Rough with prickles and glands.

*Stipules.*—Long, 1½ inches, bearded.

*Disease resistance.*—Susceptible to mildew under normal growing conditions at Somis, Calif.

Wood:

*New wood.*—Color: Reddish. Bark: Smooth.

*Old wood.*—Color: Green. Bark: Smooth.

Prickles:

*Quantity.*—Ordinary number on main canes from bases and on laterals from main canes.

*Form.*—Medium, hooked slightly downward.

*Color when young.*—Red.

Small prickles:

*Quantity.*—On main stalks: Many. On laterals: Many.

I claim:

1. A new and distinct variety of rose plant of the hybrid tea class, substantially as herein shown and described, characterized particularly as to novelty by the unique combination of its distinctive and unusual yellow-orange flower color, its moderate bloom fragrance, the profusion of glands on stipules, peduncles, leaf axils and upper rachises, vigorous upright habit growth, and large long-lasting blooms.

* * * * *

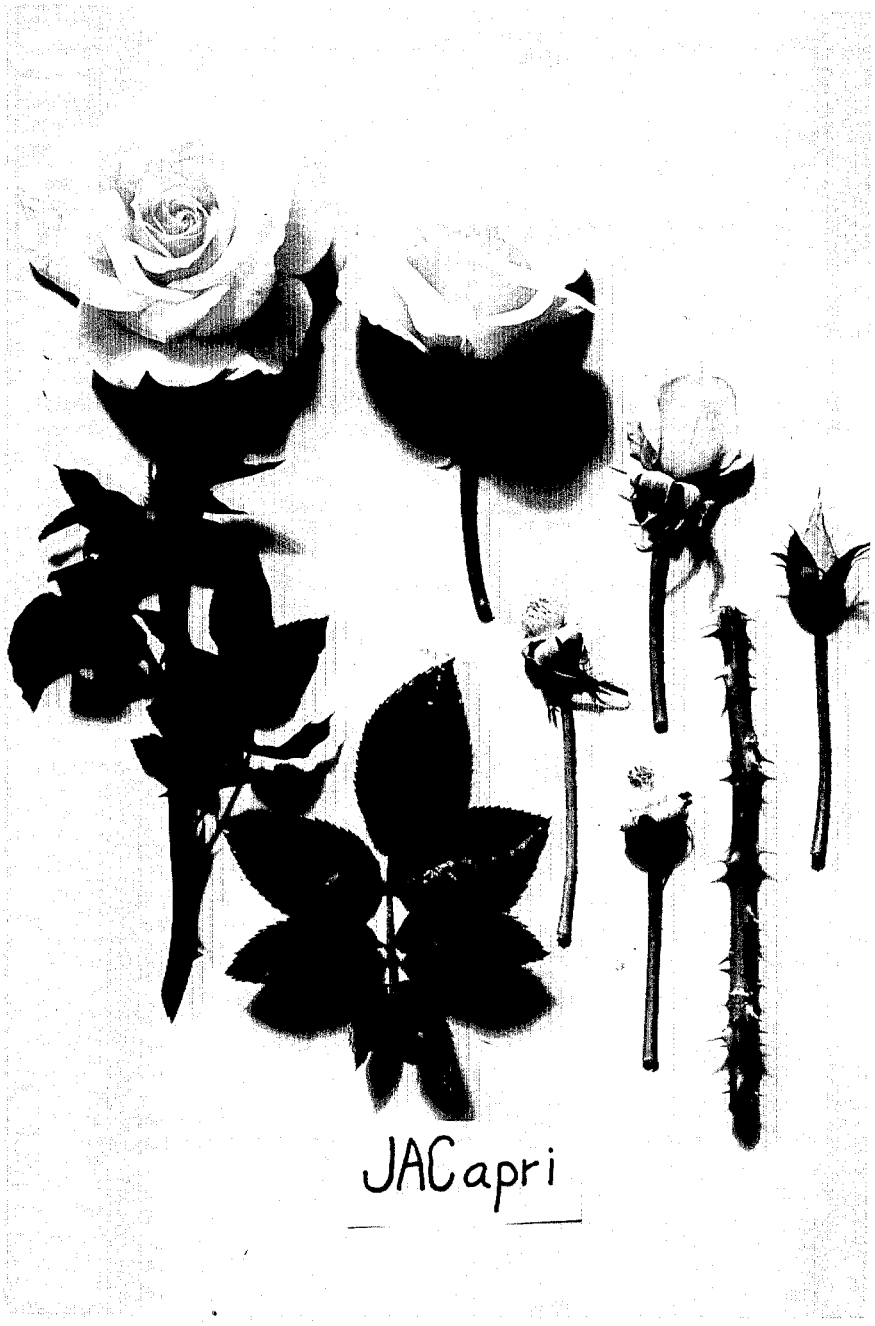
JACapri